United States Patent [19]

Hewett et al.

[11] Patent Number: 4,929,271

[45] Date of Patent: May 29, 1990

[54] HERBICIDAL METHOD USING DIFLUFENICAN

[75] Inventors: Richard H. Hewett, Thaxted; Brian M. Luscombe, Chelmsford, both of England

[73] Assignee: May & Baker Limited, Dagenham, England

[21] Appl. No.: 137,370

[22] Filed: Dec. 23, 1987

[30] Foreign Application Priority Data

Dec. 23, 1986 [GB] United Kingdom ............... 8630806

[51] Int. Cl.$^5$ ..................... A01N 43/40; A01N 37/38
[52] U.S. Cl. ............................................ 71/94; 71/116; 71/117; 71/118
[58] Field of Search ..................................... 71/94, 116

[56] References Cited

U.S. PATENT DOCUMENTS 2,396,513  2/1946  Jones ........................................ 71/116
4,618,366 10/1986  Cramp et al. ............................. 71/94

FOREIGN PATENT DOCUMENTS 2137092 10/1984 United Kingdom ................. 71/116

OTHER PUBLICATIONS

Cramp et al., "Diflufenican-A New Selective Herbicide", Brit. Crop Protect. Conf.-Weeds, (1), 23-28, 1985.

Kyndt et al., "Diflufenican-A New Herbicide for Use in Winter Cereals", Brit. Crop Protect. Confer.-Weeds, (1), 29-34, 1985.

Primary Examiner—Glennon H. Hollrah
Assistant Examiner—Susan P. Treanor
Attorney, Agent, or Firm—Burns, Doane, Swecker & Mathis

[57] ABSTRACT

The present invention relates to a method of controlling the growth of weeds at a cereal crop locus which comprises applying to the locus (a) a phenoxyalkanoic acid herbicide or an agriculturally acceptable salt or ester thereof and (b) the herbicide diflufenican, and compositions comprising these herbicides.

18 Claims, 3 Drawing Sheets

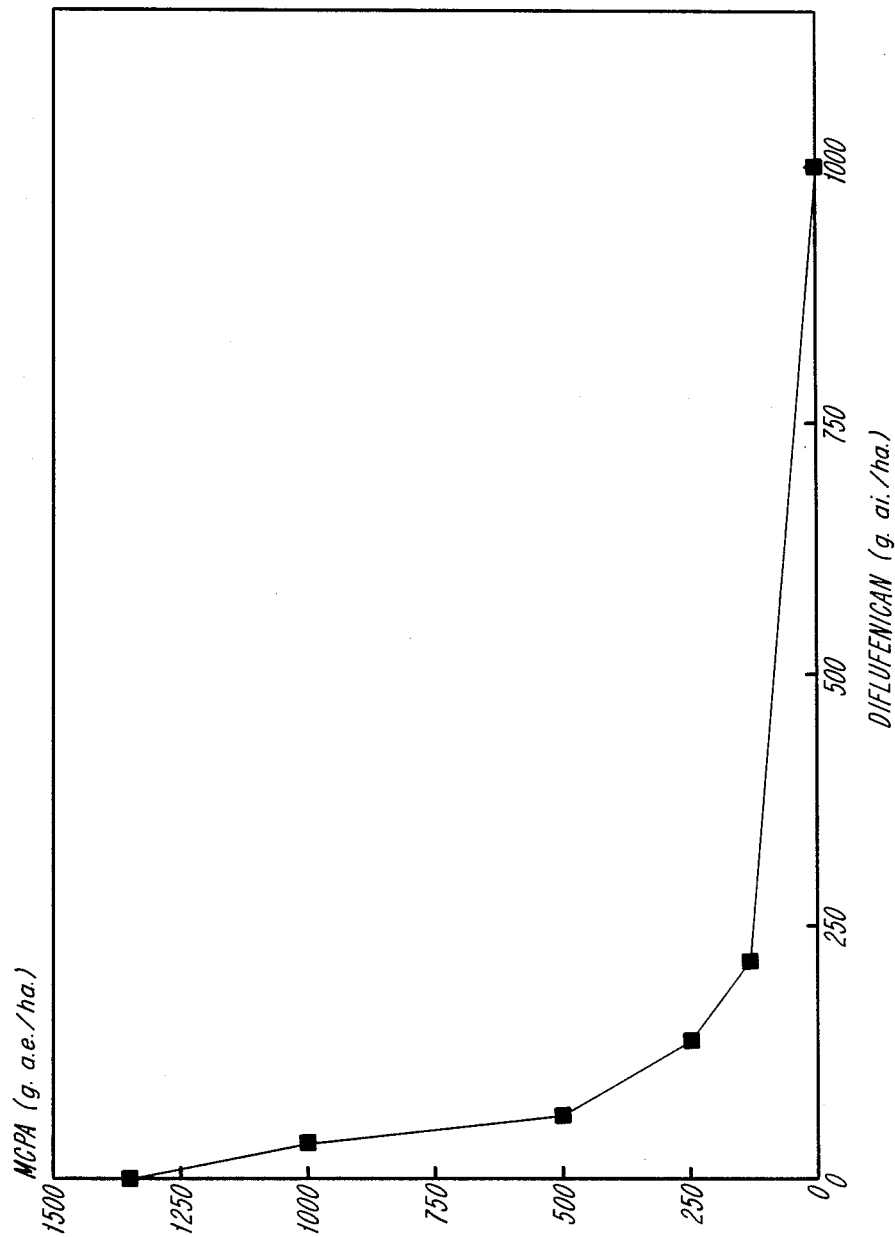

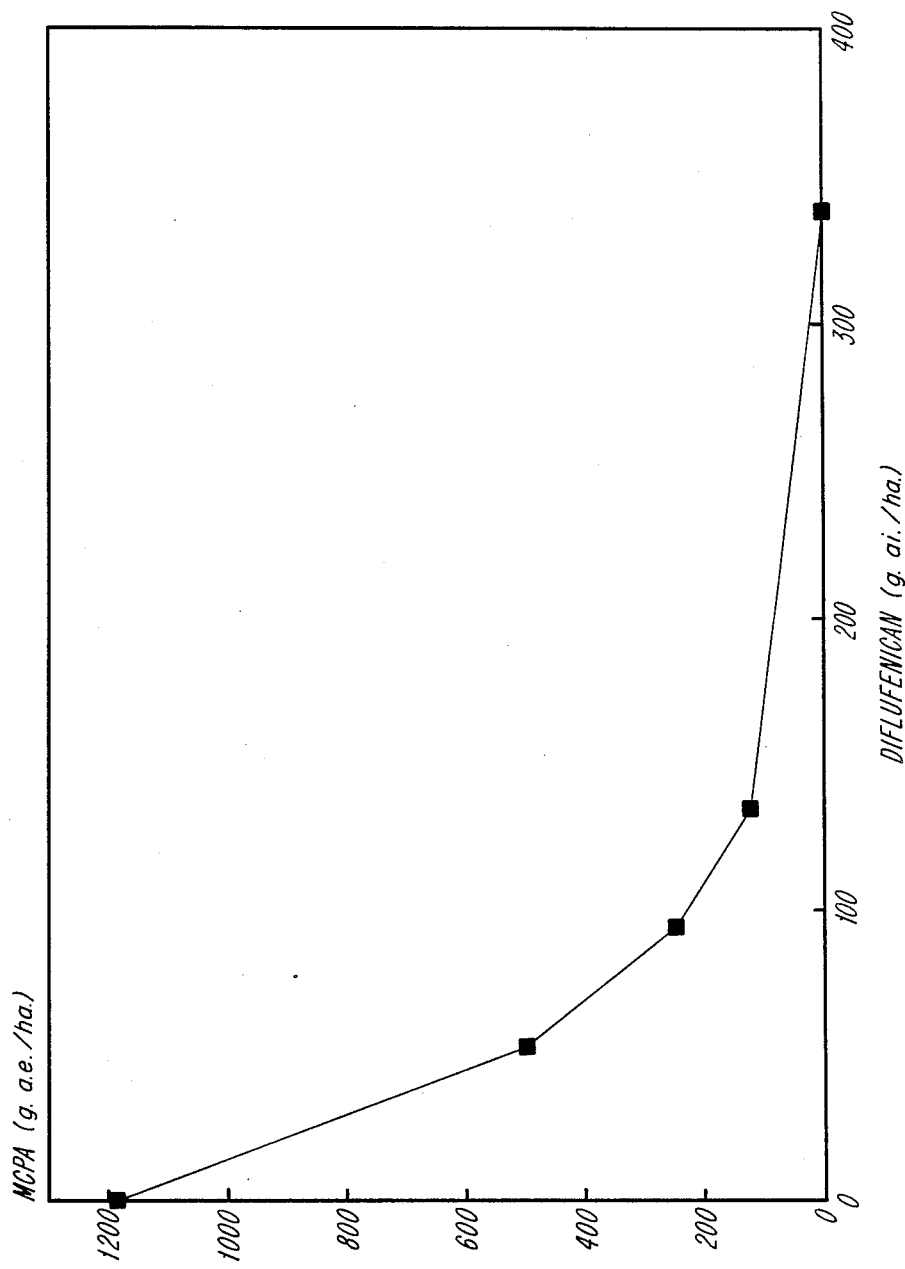

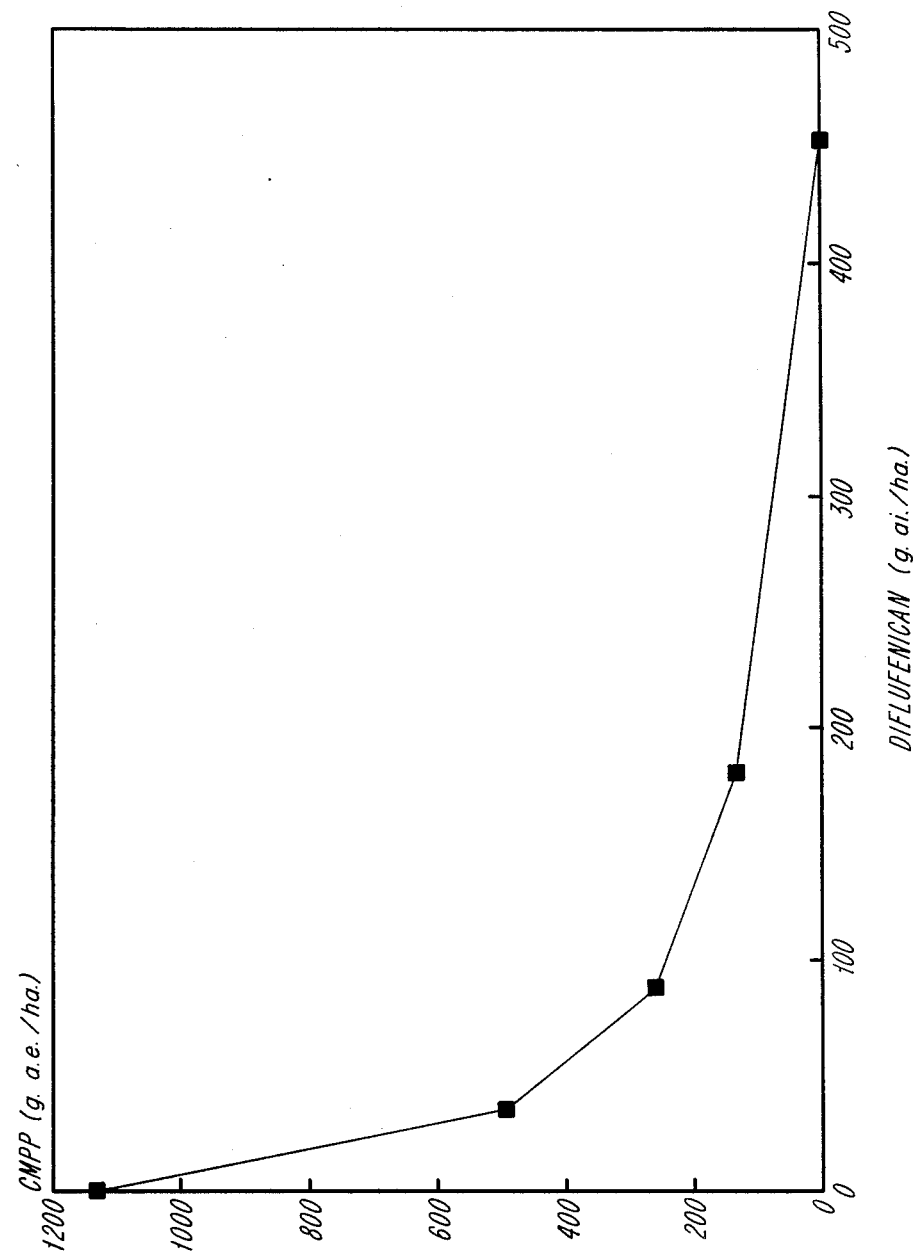

HERBICIDAL METHOD USING DIFLUFENICAN

The present invention relates to new herbicidal compositions comprising N-(2,4-difluorophenyl)-2-(3-trifluoromethylphenoxy)nicotinamide of formula I depicted hereinafter, which is disclosed in the specification of British Patent No. 2087887B as a pre- and/or post-emergence herbicide, and to their use in agriculture.

The phenoxyalkanoic acid herbicides and mixtures thereof, especially 2,4-D [2,4-dichlorophenoxyacetic acid], 2,4-DP (also known as dichlorprop) [(±)-2-(2,4-dichlorophenoxy)propionic acid], MCPA [4-chloro-2-methylphenoxyacetic acid] or CMPP (also known as mecoprop) [(±)-2-(4-chloro-2-methylphenoxy)propionic acid], are used on a large scale for post-emergence broad-leaf weed control in cereal crops.

It is to be understood that where in this specification reference is made to "a phenoxyalkanoic acid herbicide" it is intended to refer, where the context so permits, to the phenoxyalkanoic acid herbicide in the form of the parent acid (acid equivalent), or an agriculturally acceptable salt (or mixture of salts) or ester (or mixture of esters) thereof, preferably a metal or amine salt or a straight- or branched-chain alkyl ester thereof containing from 1 to 10 carbon atoms in the alkyl moiety which is optionally substituted by $C_{1-6}$-alkoxy group(s), or a mixture thereof. The invention embraces the use of a phenoxyalkanoic acid in the form of a herbicidally active enantiomer or mixture of enantiomers thereof.

Owing to short-lived residual activity in the soil the phenoxyalkanoic acid herbicides do not reliably control the weeds which emerge after application.

As a result of research and experimentation it has now been discovered that the use of the compound N-(2,4-difluorophenyl)-2-(3-trifluoromethylphenoxy)-nicotinamide (hereinafter referred to as diflufenican) in combination with a phenoxyalkanoic acid herbicide adds to their capabilities in controlling a wide spectrum of broad-leaf weeds by both foliar activity and residual soil activity.

In addition to this it has been found that the combined herbicidal activity of combinations of diflufenican with the phenoxyalkanoic acid herbicide against certain broad-leaf weed species is greater than expected when applied post-emergence (e.g. as a post-emergence spray), i.e. the herbicidal activity of combinations of diflufenican with the phenoxyalkanoic acid herbicide showed an unexpected degree of synergism [as defined by P.M.L. Tammes, Netherlands Journal of Plant Pathology, 70 (1964), pp 73–80 in a paper entitled "Isoboles, a graphic representation of synergism in pesticides"].

The remarkable synergistic effect of the mixture applied post-emergence gives improved reliability of control of weed species occurring in cereal cultures and allows for a reduction in the amount of active ingredient employed.

Accordingly the present invention provides a method for the control of the growth of weeds at a cereal crop locus which comprises applying to the locus, post-emergence of the weeds, (a) a phenoxyalkanoic acid herbicide, preferably a compound of general formula II wherein the symbol A represents a straight- or branched-chain alkylene group containing from 1 to 6 carbon atoms, $R^1$ represents a halogen, preferably chlorine, atom, a straight- or branched-chain alkyl group containing from 1 to 6 carbon atoms, preferably the methyl group, or a straight- or branched-chain alkoxy group containing from 1 to 6 carbon atoms, $R^2$ represents a halogen, preferably chlorine, atom and n is the integer 1 or 2, [more preferably MCPA or CMPP], or an agriculturally acceptable salt or ester thereof, preferably a metal or amine salt or a straight- or branched-chain alkyl ester thereof containing from 1 to 10 carbon atoms in the alkyl moiety which is optionally substituted by $C_{1-6}$-alkoxy group(s), or a mixture thereof and (b) diflufenican. Preferably the application rates are from 125 to 2500 g acid equivalent (a.e.)/ha of (a) [preferably from 125 to 500 g a.e./ha for MCPA and from 500 to 2500 g a.e./ha for CMPP] and from 25 to 250 g/ha of (b), in a ratio of (a) to (b) of 20:1 to 1:2 w/w for MCPA and from 100:1 to 2:1 w/w for CMPP. The method of the invention may be used to control a broad spectrum of weed species in cereal crops, e.g. wheat or barley by application pre- or post-emergence of the crop without significant permanent damage to the crop. The combined use described above provides both foliar and residual activity.

Preferred compounds of general formula II are 2,4-dichlorophenoxyacetic acid, (±)-2-(2,4-dichlorophenoxy)propionic acid, 4-(2,4-dichlorophenoxy)-butyric acid, 4-(4-chloro-2-methylphenoxy)butyric acid, 4-chloro-2-methylphenoxyacetic acid or (±)-2-(4-chloro-2-methylphenoxy)propionic acid, the last two of which are known respectively as MCPA and CMPP (or mecoprop), and more especially the (+)(or R)-enantiomer of CMPP.

According to a preferred feature of the invention there is provided a method for the control of weeds at a cereal crop locus which comprises the application to the locus, post-emergence of the weeds, of (a) R-CMPP or an agriculturally acceptable salt or ester thereof, preferably a metal or amine salt or a straight- or branched-chain alkyl ester thereof containing from 1 to 10 carbon atoms in the alkyl moiety which is optionally substituted by $C_{1-6}$-alkoxy group(s), and (b) diflufenican at application rates of from 250 to 1250 g acid equivalent (a.e.)/ha of (a) and from 25 to 250 g/ha of (b), in a ratio of 50:1 to 1:1 w/w of (a) to (b).

Preferred esters of the compounds of general formula II are 2-butoxyethyl, isooctyl or isopropyl.

Preferred salts of the compounds of general formula II are those with sodium, potassium or dimethylamine.

By the term 'post- emergence application', unless otherwise specified, is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil, are controlled.

Weeds that may be controlled by the method include: from broad-leaf weeds, *Abutilon theophrasti, Amaranthus retroflexus, Amsinckia intermedia, Anagallis arvensis, Anthemis arvensis, Anthemis cotula, Atriplex patula, Brassica nigra, Capsella bursa-pastoris, Chenopodium album, Cirsium arvense, Datura stramonium, Euphorbia helioscopia, Galeopsis tetrahit, Galium aparine, Lamium*

*amplexicaule, Lamium purpureum, Matricaria inodora, Myosotis arvensis, Papaver rhoeas, Plantago lanceolata, Polygonum* spp. (e.g. *Polygonum aviculare, Polygonum convolvulus* and *Polygonum persicaria), Portulaca oleracea, Raphanus raphanistrum, Senecio vulgaris, Sesbania florida, Sida spinosa, Silene alba, Sinapis arvensis, Solanum nigrum, Stellaria media, Thlaspi arvense, Urtica urens, Veronica hederifolia, Veronica persica, Viola arvensis, Xanthium* spp. (e.g. *Xanthium pennsylvanicum* and *Xanthium strumarium*).

In accordance with usual practice, a tank mix may be prepared prior to use by combining separate formulations of the individual herbicidal components, or separate formulations may be applied in a time-separated manner.

The following greenhouse experiments illustrate the present invention by demonstrating the synergistic activity of of the phenoxyalkanoic acid herbicide MCPA or CMPP and diflufenican in controlling the growth of broad-leaf weed species.

EXPERIMENT 1

Greenhouse Experiment Showing the Nature of Biological Synergism between MCPA and Diflufenican A wide range of doses of MCPA, i.e. 125, 250, 500 and 1000 g a.e. (acid equivalent)/ha (in a composition according to Example 2 as described hereinafter), and of diflufenican, i.e. 31.25, 62.5, 125, 250 and 500 g/ha (in a composition according to Example 1 as described hereinafter), were applied at a spray volume of 290 l/ha to sets of four replicate 7.5 cm square pots of loam soil each planted with 4 *Stellaria media* seedlings with 2-4 pairs of leaves or 3 *Veronica persica* seedlings at the 2-4 leaf stage. After spraying, the pots were arranged in randomised blocks in a greenhouse, watered as necessary, and assessed after 14 days for percentage phytotoxicity (reduction in green area compared with unsprayed plants)(0 =no effect, 100=complete destruction).

From these results the $ED_{90}$ values (effective dose giving 90% phytotoxicity) in grams of diflufenican per hectare, for *Stellaria media* and *Veronica persica*, were calculated for diflufenican alone and for diflufenican with increasing rates of MCPA and for MCPA alone.

The $ED_{90}$ values for *Stellaria media* were as follows:

|  | $ED_{90}$ |
| --- | --- |
| Diflufenican alone | 995 |
| Diflufenican with 125 g MCPA/ha | 217 |
| Diflufenican with 250 g MCPA/ha | 134 |
| Diflufenican with 500 g MCPA/ha | 60 |
| Diflufenican with 1000 g MCPA/ha | 33 |

The $ED_{90}$ value for MCPA alone was 1337 g a.e./ha; and the $ED_{90}$ values for *Veronica persica* were:

|  | $ED_{90}$ |
| --- | --- |
| Diflufenican alone | 339 |
| Diflufenican with 125 g MCPA/ha | 135 |
| Diflufenican with 250 g MCPA/ha | 94 |
| Diflufenican with 500 g MCPA/ha | 52 |
| Diflufenican with 1000 g MCPA/ha | less then 32 |

The $ED_{90}$ for MCPA alone was 1190 g a.e./ha.

The results were then used to plot isoboles with a "two-sided effect" according to the methods of P.M.L. Tammes, op. cit. The isoboles produced, shown hereinafter in FIGS. I and II, were clearly type III curves (Tammes, op. cit., page 75), characteristic of synergism.

EXPERIMENT 2

Greenhouse Experiment Showing the Nature of Biological Synergism between CMPP and Diflufenican A wide range of doses of CMPP, i.e. 125, 250, 500 and 100 g a.e./ha (in a composition according to Example 6 as described hereinafter), and of diflufenican i.e. 31.25, 62.5, 125, 250 and 500 g/ha (in a composition according to Example 1 as described hereinafter) were applied at a spray volume of 290 l/ha to sets of four replicate 7.5 cm square pots of loam soil each planted with 4 *Stellaria media* plants with 6 leaves and just branching.

After spraying the pots were arranged in randomised blocks in a greenhouse, watered as necessary, and assessed after 14 days for percentage phytotoxicity (reduction in green area compared with unsprayed plants) (0=no effect, 100=complete destruction).

From these results the $ED_{90}$ values in grams diflufenican per hectare for *Stellaria media* were calculated for diflufenican alone and for diflufenican with increasing rates of CMPP and for CMPP alone.

The $ED_{90}$ values for Stellaria media were as follows:

|  | $ED_{90}$ |
| --- | --- |
| Diflufenican alone | 454 |
| Diflufenican with 125 g CMPP/ha | 184 |
| Diflufenican with 250 g CMPP/ha | 88 |
| Diflufenican with 500 g CMPP/ha | 35 |
| Diflufenican with 1000 g CMPP/ha | less than 31 |

The $ED_{90}$ for CMPP alone was 1135 g a.e./ha.

The results were then used to plot an isobole with a "two-sided effect" according to the methods of P.M.L. Tammes, op. cit. The isobole produced, shown hereinafter in FIG. III, was clearly a type III curve (Tammes op. cit., page 75), characteristic of synergism.

According to a further feature of the present invention, there is provided a product comprising (a) a phenoxyalkanoic acid herbicide [preferably MCPA or CMPP] or an agriculturally acceptable salt or ester thereof, preferably a metal or amine salt or a straight- or branched-chain alkyl ester thereof containing from 1 to 10 carbon atoms in the alkyl moiety which is optionally substituted by $C_{1-6}$-alkoxy group(s), and (b) diflufenican as a combined preparation for simultaneous, separate or sequential use in controlling the growth of weeds at a cereal crop locus.

According to a feature of the present invention, there are provided compositions suitable for herbicidal use comprising (a) a phenoxyalkanoic acid herbicide or an agriculturally acceptable salt or ester thereof, preferably a metal or amine salt or a straight- or branched-chain alkyl ester thereof containing from 1 to 10 carbon atoms in the alkyl moiety which is optionally substituted by $C_{1-6}$-alkoxy group(s), and (b) diflufenican, for example in proportions of 100:1 to 1:2, preferably 20:1 to 1:2 for MCPA, 100:1 to 2:1 for CMPP and 50:1 to 1:1 for R-CMPP, w/w in association with, and preferably homogeneously dispersed in, a herbicidally-acceptable diluent or carrier and/or surface-active agent. Suitable diluents or carriers or surface-active agents are of the type generally accepted in the art as being suitable for use in herbicidal compositions and which are compatible with the phenoxyalkanoic acid herbicide and diflufenican. The term "homogeneously dispersed" is used to include compositions in which the phenoxyalkanoic acid herbicide and diflufenican are dissolved in the other components. The term "herbicidal compositions" is used in a broad sense to include not only compositions which are ready for use as herbicides but also concentrates which must be diluted before use. Preferably, the compositions contain from 0.05 to 90% by weight of the phenoxyalkanoic acid herbicide and diflufenican.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, products based on condensates of ethylene oxide with nonyl- or octyl- phenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl- sodium sulphono-succinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the phenoxyalkanoic acid herbicide and diflufenican with solid diluents or by impregnating the solid diluents or carriers with solutions of the phenoxyalkanoic acid herbicide and diflufenican in volatile solvents, evaporating the solvents and, if necessary, grinding the products so as to obtain powders. Granular formulations may be prepared by absorbing the phenoxyalkanoic acid herbicide and diflufenican (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the phenoxyalkanoic acid herbicide and diflufenican may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of the phenoxyalkanoic acid herbicide and diflufenican, from 2 to 10% w/v of surface-active agent, from 0.1 to 5% w/v of thickener and from 15 to 87.9% by volume of water; wettable powders which comprise from 10 to 90% w/w of the phenoxyalkanoic acid herbicide and diflufenican, from 2 to 10% w/w of surface-active agent and from 8 to 88% w/w of solid diluent or carrier; liquid water soluble concentrates which comprise from 10 to 30% w/v of the phenoxyalkanoic acid herbicide and diflufenican, from 5 to 25% w/v of surface-active agent and from 45 to 85% by volume of water-miscible solvent, e.g. dimethylformamide; liquid emulsifiable suspension concentrates which comprise 10 to 70% w/v of the phenoxyalkanoic acid herbicide and diflufenican, from 5 to 15% w/v of surface-active agent, from 0.1 to 5% w/v of thickener and from 10 to 84.9% by volume of organic solvent; granules which comprise from 2 to 10% w/w of the phenoxyalkanoic acid herbicide and diflufenican, from 0.5 to 2% w/w of surface-active agent and from 88 to 97.5% w/w of granular carrier and emulsifiable concentrates which comprise from 0.05 to 90% w/v, and preferably from 1 to 60% w/v, of the phenoxyalkanoic acid herbicide and diflufenican, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the phenoxyalkanoic acid herbicide and diflufenican in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example bifenox [methyl 5-(2,4-dichlorophenoxy)-2-nitrobenzoate], chlortoluron [N'-(3-chloro-4-methylphenyl)-N,N-dimethylurea], cyanazine [2-chloro-4-(1-cyano-1-methylethylamino)-6-ethylamino-1,3,5-triazine], isoproturon [N'-(4-isopropylphenyl)-N,N-dimethylurea], linuron [N'-(3,4-dichlorophenyl)-N-methoxy-N-methylurea], methabenzthiazuron [N-(benzothiazol-2-yl)-N,N'-dimethylurea], hydroxybenzonitriles, e.g. ioxynil and bromoxynil; insecticides, e.g. carbaryl [naphth-1-yl N-methylcarbamate] and synthetic pyrethroids, e.g. permethrin and cypermethrin;

and fungicides, e.g. 2,6-dimethyl-4-tridecyl-morpholine, methyl N-(1-butylcarbamoylbenzimidazol-2-yl)carbamate, 1,2-bis-(3-methoxycarbonyl-2-thioureido)benzene, isopropyl 1-carbamoyl-3-(3,5-dichlorophenyl)-hydantoin and 1-(4-chlorophenoxy)-3,3-dimethyl-1-(1,2,4-triazol1-yl)butan-2-one. Other biologically active materials which may be included in, or used in conjunction with, the herbicidal compositions of the present invention are plant growth regulators, e.g. (2-chloroethyl)trimethylammonium chloride and 2-chloroethanephosphonic acid; and fertilizers containing, for example, nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The compositions of the invention may be made up as an article of manufacture comprising the phenoxyalkanoic acid herbicide and diflufenican and optionally other biologically active compounds as hereinbefore described or, as is preferred, a herbicidal composition as hereinbefore described, and preferably a herbicidal concentrate which must be diluted before use, comprising the phenoxyalkanoic acid herbicide and diflufenican within a container for the aforesaid phenoxyalkanoic acid herbicide and diflufenican or a said herbicidal composition, and instructions physically associated with the aforesaid container setting out the manner in which the aforesaid phenoxyalkanoic acid herbicide and diflufenican or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least 0.5 hectares of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application from 125 g to 2500 g a.e. of the phenoxyalkanoic acid herbicide and from 25 g to 250 g of diflufenican per hectare in the manner and for the purposes hereinbefore described.

The following Examples illustrate herbicidal compositions according to the present invention.

EXAMPLE 1

An aqueous suspension concentrate was made from:

| | |
|---|---|
| diflufenican | 50% w/v |
| propylene glycol | 5% w/v |
| Olin 10 G (para-nonylphenoxy polyglycidol) | 0.67% w/v |
| Soprophor FL (triethanolamine salt of oxyethylated polyarylphenolphosphate) | 1.33% w/v |
| Antifoam FD (silicone antifoam) | 0.01% v/v |
| Rhodigel 23 (xanthan gum) | 0.2% w/v |
| dichlorophen sodium solution, 40% w/w | 0.25% w/v |
| water | to 100% by volume | by blending the diflufenican with an aqueous solution of the Soprophor FL, Antifoam FD and Olin 10 G and milling through a bead-mill. An aqueous solution of the Rhodigel 23, dichlorophen sodium solution and propylene glycol is then blended with the milled slurry and made up to volume with water.

EXAMPLE 2

An aqueous solution containing potassium, sodium and dimethylamine salts of MCPA equivalent to 500 g/l of MCPA was formed by dissolving the potassium, sodium and dimethylamine salts of MCPA in water.

EXAMPLE 3

An (1:20) emulsifiable concentrate was formed from:

| | |
|---|---|
| diflufenican | 2% w/v |
| MCPA as the isooctyl ester | 40% w/v |
| Soprophor BSU (tristyryl phenol/ ethylene oxide condensate containing 18 moles of ethylene oxide) | 3% w/v |
| Arylan CA (calcium dodecyl benzene sulphonate 70% solution in butanol) | 5% w/v |
| cyclohexanone | 25% w/v |
| Solvesso 150 (aromatic C10 petroleum fraction) | to 100% by volume | by adding with stirring the diflufenican and MCPA isooctyl ester to a solution of the Soprophor BSU and Arylan CA in the cyclohexanone. When fully dissolved, Solvesso 150 is added to volume.

1.25 liters of the resulting formulation were diluted in 200 liters of water and applied post-emergence to 1 hectare of spring wheat to control *Sinapis arvensis* and *Raphanus raphanistrum*.

EXAMPLE 4

A 1:2 mixture was formed by tank mixing 0.25 l of the composition of Example 2 with 500 ml of the composition of Example 1 in a volume of 200 l of water. The resulting spray fluid was applied to one hectare of winter wheat to control *Stellaria media* and *Veronica persica*.

EXAMPLE 5

A 2:1 mixture was formed by tank mixing 877 ml of the composition of Example 6 with 500 ml of the composition of Example 1 in a volume of 200 l of water. The resulting spray fluid was applied to one hectare of winter wheat to control *Viola arvensis, Veronica hederifolia* and *Galium aparine*.

EXAMPLE 6

An aqueous solution containing 570 g/l CMPP as the potassium salt was formed by dissolving the CMPP potassium salt in water.

EXAMPLE 7

A 100:1 mixture was formed by tank mixing 4386 ml of the composition of Example 6 with 50 ml of the composition of Example 1 in a volume of 500 l/ha. The resulting spray fluid was applied to one hectare of winter barley to control *Stellaria media, Galium aparine* and *Viola arvensis.*

In the mixed formulations in the Examples described hereinbefore, the phenoxyalkanoic acid herbicide may be replaced by the appropriate quantities of other phenoxyalkanoic acid herbicides.

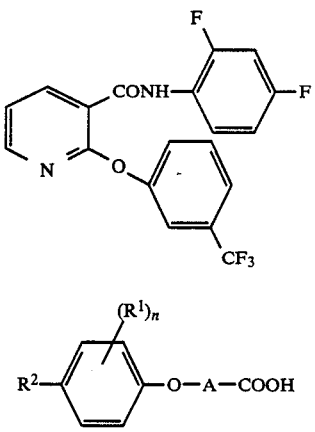

We claim:

1. A method of controlling the growth of weeds at a cereal crop locus which comprises applying to the locus, post-emergence of the weeds, an effective amount of (a) a phenoxyalkanoic acid herbicide selected from the group consisting of MCPA and CMPP or an agriculturally acceptable salt or ester thereof at an application rate of from 125 g to 250 g a.e. per hectare, and (b) diflufenican, which is N-(2,4-difluorophenyl)-2-(3-trifluromethyl-phenoxy)-nicotinamide at an application rate of from 25 g to 250 g per hectare.

2. A method according to claim 1 in which the phenoxyalkanoic acid herbicide is R-CMPP.

3. A method according to claim 1 in which (a) is a metal or amine salt of the phenoxyalkanoic acid herbicide.

4. A method according to claim 1 in which (a) is a straight- or branched-chain alkyl ester of the phenoxyalkanoic acid herbicide of 1 to 10 carbon atoms in the alkyl moiety which is optionally substituted by $C_{1-6}$-alkoxy group(s).

5. A method according to claim 1 which comprises the application of (a) MCPA or an agriculturally acceptable salt or ester thereof and (b) diflufenican at application rates of from 125 to 250 g a.e./ha and from 25 to 250 g/ha, respectively, in a ratio of 20:1 to 1:2 by weight.

6. A method according to claim 1 which comprises the application of (a) CMPP or an agriculturally acceptable salt or ester thereof and (b) diflufenican at application rates of from 125 to 250 g a.e./ha and from 25 to 250 g/ha, respectively, in a ratio of 100:1 to 2:1 by weight.

7. A method according to claim 1 which comprises the application of (a) R-CMPP or an agriculturally acceptable salt or ester thereof and (b) diflufenican at application rates of from 125 to 250 g a.e./ha and from 25 to 250 g/ha, respectively, in a ratio of 50:1 to 1:1 by weight.

8. A product comprising an effective amount of (a) a phenoxyalkanoic acid herbicide selected from the group consisting of MCPA and CMPP or an agriculturally acceptable salt or ester thereof and (b) diflufenican, which is N-(2,4-difluorophenyl)-2-(3-trifluoromethyl-phenoxy)-nicotinamide, as a preparation for simultaneous, separate or sequential use in controlling the growth of weeds at a cereal crop locus.

9. A product according to claim 8 in which (a) is a metal or amine salt of the phenoxyalkanoic acid herbicide.

10. A product according to claim 8 in which (a) is a straight- or branched-chain alkyl ester of the phenoxyalkanoic acid herbicide of 1 to 10 carbon atoms in the alkyl moiety which is optionally substituted by $C_{1-6}$-alkoxy group(s).

11. A herbicidal composition which comprises an effective amount of (a) a phenoxyalkanoic acid herbicide selected from the group consisting of MCPA and CMPP or an agriculturally acceptable salt or ester thereof and (b) diflufenican, which is N-(2,4-difluorophenyl)-2-(3-trifluoromethylphenoxy)-nicotinamide, in association with a herbicidally acceptable diluent or carrier and/or surface active agent.

12. A herbicidal composition according to claim 11 in which the acid equivalent weight ratio of (a) to (b) is 100:1 to 1:2 by weight.

13. A herbicidal composition according to claim 11 which comprises from 0.05 to 90% by weight of diflufenican and phenoxyalkanoic acid herbicide.

14. A herbicidal composition according to claim 11 in which (a) is MCPA and the acid equivalent weight ratio of (a) to (b) is 20:1 to 1:2 by weight.

15. A herbicidal composition according to claim 11 in which (a) is CMPP and the acid equivalent weight ratio of (a) to (b) is 100:1 to 2:1 by weight.

16. A herbicidal composition according to claim 11 in which (a) is R-CMPP and the acid equivalent weight ratio of (a) to (b) is 50:1 to 1:1 by weight.

17. A herbicidal composition according to claim 11 in which (a) is the metal or amine salt of a phenoxyalkanoic acid herbicide.

18. A herbicidal composition according to claim 11 in which (a) is a straight- or branched-chain alkyl ester of the phenoxyalkanoic acid herbicide of 1 to 10 carbon atoms in the alkyl moiety which is optionally substituted by $C_{1-16}$-alkoxy group(s).

* * * * *